United States Patent [19]

Kocal et al.

[11] Patent Number: 5,849,977
[45] Date of Patent: Dec. 15, 1998

[54] METAL CATION-MODIFIED ALKYLATION CATALYSTS

[75] Inventors: Joseph A. Kocal, Gurnee; Anil R. Oroskar, Downers Grove, both of Ill.

[73] Assignee: UOP, Des Plaines, Ill.

[21] Appl. No.: 630,318

[22] Filed: Apr. 10, 1996

Related U.S. Application Data

[63] Continuation-in-part of Ser. No. 330,950, Oct. 28, 1994, abandoned, which is a continuation-in-part of Ser. No. 93,150, Jul. 19, 1993, abandoned.

[51] Int. Cl.$^6$ ..................................................... C07C 2/58
[52] U.S. Cl. ........................ 585/729; 585/727; 585/728; 585/729; 502/230; 502/229; 502/231; 502/304; 502/330; 502/328; 502/341; 502/346; 502/348; 502/349; 502/227
[58] Field of Search ..................................... 502/304, 227, 502/346, 348, 349; 585/729, 726, 727, 728, 721

[56] References Cited

U.S. PATENT DOCUMENTS

| | | | |
|---|---|---|---|
| 2,972,649 | 2/1961 | Thomas et al. | 260/683.53 |
| 2,999,074 | 9/1961 | Bloch et al. | 252/442 |
| 3,113,988 | 12/1963 | Meisinger | 260/683.53 |
| 3,318,820 | 5/1967 | Muller et al. | 252/415 |
| 5,310,713 | 5/1994 | Kojima et al. | 502/30 |
| 5,391,527 | 2/1995 | Kojima et al. | 502/53 |

OTHER PUBLICATIONS

B.R. Shah in "Handbook of Petroleum Refining Processes", R.A. Meyers, editor, McGraw–Hill Book Company, 1986, pp. 1–3 through 1–28.

Primary Examiner—Glenn Caldarola
Assistant Examiner—Tanaga A. Boozer
Attorney, Agent, or Firm—Thomas K. McBride; Eugene I. Snyder

[57] ABSTRACT

A process for the alkylation of alkenes having from 2 to 6 carbon atoms with an alkane having from 4 to 6 carbon atoms to afford an alkylate comprises reacting in the liquid phase the alkene and alkane under alkylation conditions in the presence of a novel catalyst comprising: a) a refractory inorganic oxide, b) the reaction product of a first metal halide and bound surface hydroxyl groups of the refractory inorganic oxide, c) a second metal cation, and d) optionally a zerovalent third metal. The refractory inorganic oxide is selected form the group consisting of alumina, titania, zirconia, chromia, silica, boria, silica-alumina, and combinations thereof and the first metal halide is a fluoride, chloride, or bromide of aluminum or boron. The second metal cation is selected from the group consisting of: monovalent metal cations in an amount from 0.0026 up to about 0.20 gram atoms per 100 grams refractory inorganic oxide for lithium, potassium, cesium, rubidium, silver, and copper, and from 0.012 to about 0.12 gram atoms for sodium; and alkaline earth metal cations in an amount from about 0.0013 up to about 0.01 gram atoms per 100 grams of refractory inorganic oxide for beryllium, strontium, and barium, and in an amount from about 0.004 up to about 0.1 gram atoms per 100 grams support for magnesium and calcium, or combinations thereof. The third metal is selected from the group consisting of platinum, palladium, nickel ruthenium, rhodium, osmium and iridium, and any combination thereof.

16 Claims, No Drawings

5,849,977

METAL CATION-MODIFIED ALKYLATION CATALYSTS

CROSS REFERENCE TO RELATED APPLICATION

This application is a continuation-in-part of our application, U.S. Ser. No. 08/330,950 filed Oct. 28, 1994, now abandoned, which is a continuation-in-part of our application, U.S. Ser. No. 08/093,150, filed Jul. 19, 1993, now abandoned, all of which is incorporated herewith.

BACKGROUND OF THE INVENTION

Even in the era of anti-knock additives such as tetraethyl lead, the use of alkylate as a component in motor fuel gained both universal acceptance and importance. In the ensuing years alkylate has become an even more important component of motor fuel. Alkylate is an economical, clean-burning, high-octane, low volatility product that is becoming increasingly important as the composition of gasoline changes in response to environmental concerns and legislation. The governmental regulations most applicable to the increasing importance of alkylates are those affecting lead and butane. Adding lead anti-knock compounds was the easiest way to raise gasoline octane, but because of continuing concerns over the effects of lead emissions the phasing out of lead in gasoline was required, a process over 90% complete. Butane is another effective octane-booster but tends to evaporate from gasoline, especially in warm weather, contributing to smog formation. Recent EPA regulations have effected their virtually complete removal from gasoline.

The term "alkylate" generally refers to a complex mixture resulting from the alkylation of C2–C6 olefins present or formed in a feedstream with intermediates arising primarily from alkanes, especially branched alkanes, and predominantly those with 4 carbon atoms, especially isobutane, also present in the same feedstream. It is most desirable that the complex product mixture from C4 olefins and alkanes, referred to as alkylate, contains predominantly trimethylpentanes, since these are high-octane components which add considerable value to motor fuel, yet the chemistry of alkylation affords a dazzling variety of products resulting from only a few basic chemical reactions characteristic of the carbonium ion which plays a central role in the alkylation process. Thus, chain transfer (intermolecular hydride transfer and alkyl shifts), oligomerization and disproportionation serve to place into the alkylate as byproduct materials of from 5–12+ carbon atoms from a feed containing only C4 olefins and C4 alkanes.

The alkylation of olefins is catalyzed by strong acids generally. Although such alkylation has been the focus of intense and continuing scrutiny for several decades, the requirements of optimum selectivity while achieving high conversion have heretofore narrowed, for all practical purposes, the commercial choice of catalyst to sulfuric acid and liquid hydrogen fluoride. While processes based on each of these acids have gained commercial acceptance those based on HF have been favored at least in part because of the relative ease of HF regeneration. A brief but valuable overview of HF-catalyzed aklation is presented by B. R. Shah in "Handbook of Petroleum Refining Processes", R. A. Meyers, editor, McGraw-Hill Book Company, 1986, pp 1–3 through 1–28.

In a rather over-simplified description, the HF-catalyzed alkylation process is carried out as follows. Olefinic and isobutane feedstocks are combined and mixed with HF in an alkylation reaction zone. The reactor effluent is separated into the desired alkylate, acid, and other light gases which are predominantly unreacted isobutanes. The HF is either recycled to the reactor directly or regenerated, in whole or in part, prior to its being recycled to the reactor. Unreacted isobutane also is recycled to the reactor, and the alkylate is then used in motor fuel blending.

Recently HF (hydrofluoric acid) has come under environmental pressure. Hydrofluoric acid is classified as an Acutely Hazardous Material, and in Southern California the Board of the South Coast Air Quality Management District recently required that the use of HF in alkylation be phased out by Jan. 1, 1998. Consequently there is increasing reason to seek substitutes for HF as an alkylation catalyst for alkylate production. It is quite desirable to have a solid acid as an effective catalyst, for this permits development of fixed bed processes, a desirable alternative in the petroleum refining industry.

One of the promising solid catalysts for alkylation of C2–C6 olefins with alkanes in the 4 to 6 carbon range, a process hereafter specifically referred to as motor fuel alkylation, is the reaction product between one or more of the metal halides active as Friedel-Crafts catalysts and a refractory inorganic oxide having surface hydroxyl groups, where the refractory inorganic oxide also contains dispersed thereon a metal having hydrogenation activity for olefins. Such catalysts are reasonably well known in the art, as exemplified by U.S. Pat. No. 2,999,074, and includes, for example, the reaction product of aluminum chloride and alumina containing zerovalent platinum. However, such catalysts suffer from several disadvantages which preclude the development of a motor fuel alkylation process based on their use as an alkylation catalyst. One disadvantage is that the materials are too acidic, effecting not only the desired alkylation but also concurrently effecting cracking of some of the various alkylate components. Another disadvantage of these catalysts is that they are insufficiently selective, a characteristic which also likely arises from "excess" acidity.

Although the terms "cracking" and "selectivity" in the context of paraffin alkylation, and especially in motor fuel alkylation, are well known to the skilled artisan, it may be well to define them here so as to preclude any confusion. By "cracking" is meant the acid-catalyzed degradation of various components formed in the alkylation to products of lower molecular weight and lower carbon number. An example would be the tendency of C8 alkylate products to decompose into a C5 and a C3 product. The term "selectivity" is a measure of the extent of monoalkylation in comparison with multiple alkylation. For example, it is most desirable that the olefin react only with the alkanes initially in the feedstocks. However, in practice some of the alkylation products formed also subsequently react with the alkene in the feedstock to form secondary alkylation products. Thus, for example, if the feedstock contains only butanes and butenes, the primary alkylation product would be a C8 hydrocarbon and secondary alkylation products would be C12, C16, and so forth. The secondary alkylation products themselves can be cracked to afford lower molecular weight hydrocarbons. Selectivity is the measure of monoalkylation relative to all types of alkylation which may occur. Another side reaction desired to be avoided is oligomerization, which leads to inefficient olefin consumption.

What we have discovered is that if composites of the type referred to above are modified by impregnation with certain metal cations, evidently their acidity is sufficiently modified to significantly reduce the extent of cracking while significantly increasing selectivity where the composite is used as a catalyst in motor fuel alkylation. The resulting alkylate shows a dramatic increase in octane number and a continuous process for motor fuel alkylation based on the catalysts of our invention becomes commercially feasible.

SUMMARY OF THE INVENTION

A purpose of this invention is to provide a composite which effectively catalyzes the alkylation of alkenes with alkanes with decreased cracking and increased selectivity relative to prior art solid acid catalysts. An embodiment is a catalytic composite of a refractory inorganic oxide impregnated with a monovalent cation, especially an alkali metal cation, or an alkaline earth metal cation, and whose bound surface hydroxyl groups have reacted, at least in part, with a metal halide of the Friedel-Crafts type. In a specific embodiment the refractory inorganic oxide is alumina and the Friedel-Crafts type metal halide is aluminum chloride. In yet another specific embodiment the refractory inorganic oxide is impregnated with potassium. In still another specific embodiment the composite also is impregnated with a metal such as platinum, palladium, or nickel. In a further embodiment the refractory inorganic oxide is an aluminum phosphate. Other purposes and embodiments are further elaborated on within.

DESCRIPTION OF THE INVENTION

What we have found is that when composites which are the reaction product of a Friedel-Crafts type metal halide and the bound surface hydroxyl groups of refractory inorganic oxide are modified by impregnation with certain cations, especially those of an alkali or alkaline earth metal, the resulting composite effects the alkylation of alkenes by alkanes to afford as the product an alkylate with excellent properties as evidenced by octane number. In particular, the resulting alkylate exhibits a significant octane number increase relative to the alkylate formed from a similar catalyst which has not been impregnated with the metal cations of this invention. Our observation permits the development of the solid bed alkylation process based on our composite, and this is the invention which we now describe in detail.

The feedstocks of our invention are mixtures of alkanes and alkenes. The alkanes which may be used contain from 4 to 6 carbon atoms and the branched alkanes are particularly useful in the practice of our invention. Suitable alkanes are illustrated by n-butane, 2-methylpropane (commonly called isobutane), 2-methylbutane (or isopentane), 2,2-dimethylpropane (neopentane), n-pentane, n-hexane, 2,3-dimethylbutane, 2-methylpentane, 3-methylpentane, and 2,2-dimethylbutane.

The alkenes which are used in the practice of our invention contain from 2 to 6 carbon atoms and are ethylene, propylene, the butenes, the pentenes, and the hexenes. Internal alkenes are favored over the terminal alkenes, and a particularly desirable alkene is butene-2. The feedstock is a mixture of one or more alkanes and one or more alkenes where the total alkane/alkene ratio may be as high as 100:1 and as low as 1:1, although the range between 20:1 through 5:1 is much more usual.

The analogs of our catalyst without the metal cations of our invention are well known in the art (see U.S. Pat. No. 2,999,074; cf. 3,318,820) and the extensive descriptions of their preparations are applicable to our catalyst with the exception of impregnation with a monovalent cation or alkaline earth metal cation. Thus, much of the prior art description is applicable to our catalysts and makes a detailed description of their preparation unnecessary. The following description then will suffice merely to afford the reader an understanding of our invention.

The refractory inorganic oxides suitable for use in this invention have a surface area of at least about 35 $m^2/g$, preferably greater than about 50 $m^2/g$, and more desirably greater than 100 $m^2/g$. There appears to be some advantage to working with materials having as high a surface area as possible, although exceptions are known which preclude making this a general statement. Suitable refractory inorganic oxides include alumina, titania, zirconia, chromia, silica, boria, silica-alumina, aluminum phosphate, and combinations thereof. Of these alumina is particularly preferred. Any alumina phase may be used so long as it has a surface area of at least 35 $m^2/g$ and has surface hydroxyl groups, which for all practical matters excludes alpha-alumina. Among the phases which may be used are included gamma-, etc-, and theta-alumina, although the various phases are not necessarily equivalent in their effectiveness as a motor fuel alkylation catalyst. Aluminum phosphate is another favored refractory material.

It is required that the refractory inorganic oxide have bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of adsorbed water is generally detrimental to the preparation of the catalysts of our invention, the refractory inorganic oxides are first treated to remove surface hydroxyl groups arising from water, most usually by calcination at a temperature which specifically and preferentially removes physically adsorbed water without chemically altering the other hydroxyl groups. For example, calcination temperatures ranging from about 350° C. to about 700° C. are usually satisfactory where the inorganic oxide is alumina.

The catalytic composites of our invention optionally contain a metal having hydrogenation activity. Where a hydrogenation-active metal is present it generally is deposited on the refractory inorganic oxide prior to the reaction of its bound surface hydroxyl groups with metal halides. Although such a procedure has proven both convenient and effective, we do not wish to imply that this is the only sequence which may be used to afford an effective catalyst. Metals which have been found to be particularly effective include nickel and the noble metals of platinum, palladium, ruthenium, rhodium, osmium, and iridium, although platinum and palladium are by far the most desirable of the noble metals. The desired metal may be composited with the refractory inorganic oxide in any desired manner, such as by impregnation, coprecipitation, dipping, and so forth, of a suitable salt followed by reduction of the metal to its zerovalent state. Such methods are well known and need not be described here. Hydrogenation-active metal levels may range between about 0.01 up to about 1.0 weight percent for the noble metals, based on the weight of the finished catalyst, and from about 0.1 up to about 5 weight percent for nickel. The composite of the metal and refractory inorganic oxide is dried and calcined under controlled conditions to remove physically adsorbed water but under sufficiently mild conditions so that the "chemically combined" hydroxyl groups are not eliminated.

The more usual way of introducing a hydrogenation-active metal into the catalytic composites of our invention is by coimpregnation of the refractory inorganic oxide with a salt of the hydrogenation-active metal together with one or more monovalent or alkaline earth metal cations of our invention. But as stated above it is not believed that the particular procedure or sequence used is determinative of success of, or even of substantial significance to, the final catalytic composite.

The next stage in the preparation of our catalytic composites, whether or not a metal with hydrogenation activity has been deposited thereon, is to deposit on the composite one or more monovalent metal or alkaline earth metal cations. Such metals include lithium, sodium, potassium, cesium, rubidium, silver, copper(I), beryllium, magnesium, calcium, strontium, and barium. Among the monovalent metal cations the alkali metal cations are favored. The amount of metal cation which is impregnated on the composite is in most cases an amount having a gram atom equivalent from about 0.1 up to about 8 weight percent potassium, which is 0.0026 gram atoms potassium up to 0.2 gram atoms per 100 gram support. We define a "gram atom equivalent" of another metal cation as being a number of gram atoms of the metal divided by its valence per 100 grams support. For example, for most divalent atoms the gram atom equivalent is 0.0013 up to about 0.1 gram atoms per 100 gram support.

There is some irregularity in the amount of metal cations which are to be impregnated upon the refractory inorganic oxides which are the supports in our invention. For the monovalent cations of lithium, potassium, cesium, rubidium, silver and copper, the amounts deposited are from 0.0026 to about 0.20 gram atom per 100 grams support; for sodium the amount is from 0.009 to about 0.20 gram atom per 100 grams support. For the divalent cations beryllium, strontium, and barium the amount is from 0.0013 to about 0.1 gram atoms per 100 gram support; for magnesium and calcium the amount is from 0.004 to about 0.1 gram atoms per 100 gram support. These amounts in terms of grams of metal cation per 100 gram support are summarized in the following table. Since the preferred range is from 0.012 up to about 0.12 gram atoms for monovalent cations, and 0.006 up to about 0.06 gram atoms for divalent metal cations, the preferred ranges also are listed in the following table. It needs to be emphasized that in all cases the minimum amount of cation added is well outside that normally found as impurities in the supports of our invention, hence will not be present incidental to their preparation.

TABLE

Amounts of Metal Cations on Supports (grams per 100 gram support)

| Metal Cation | Range | | Preferred Range | |
|---|---|---|---|---|
| | Minimum | Maximum | Minimum | Maximum |
| Monovalent | | | | |
| Lithium | 0.02 | 1.4 | 0.1 | 0.8 |
| Sodium | 0.2 | 4.6 | 0.3 | 2.8 |
| Potassium | 0.1 | 7.8 | 0.5 | 4.7 |
| Cesium | 0.3 | 26.6 | 1.6 | 15.9 |
| Rubidium | 0.2 | 17.1 | 1.0 | 10.3 |
| Copper (I) | 0.2 | 12.7 | 0.8 | 7.6 |
| Silver | 0.3 | 21.6 | 1.3 | 12.9 |
| Divalent | | | | |
| Beryllium | 0.01 | 0.9 | 0.1 | 0.5 |
| Magnesium | 0.1 | 2.4 | 0.1 | 1.5 |
| Calcium | 0.2 | 4.0 | 0.2 | 2.4 |
| Strontium | 0.1 | 8.8 | 0.5 | 5.3 |
| Barium | 0.2 | 13.7 | 0.8 | 8.2 |

Impregnation of the composite by the monovalent metal or alkaline earth metal cation may be done simply by mixing the composite with a suitable aqueous solution of the salt and removing water. The particular monovalent or alkaline earth metal salt used is not especially important so long as it provides sufficient solubility in water. As a practical matter, the halides, nitrates, and acetates may be the most commonly employed salts. Salts prone to precipitation should be avoided in order to avoid non-uniform impregnation, but otherwise there are no serious limitations on the salts which may be used. After evaporation of excess water, materials generally are dried at a temperature between about 100° and 200° C. for 2–4 hours and then calcined at a temperature which specifically and preferentially removes physically adsorbed water without chemically altering the other hydroxyl groups. As mentioned before, temperatures ranging from about 350° C. to about 700° C. usually are satisfactory where the inorganic oxide is alumina.

Subsequent to metal deposition and calcination, the bound surface hydroxyl groups of the refractory inorganic oxide are reacted with a metal halide having Friedel-Crafts activity. Among the metals which may be used are included aluminum, zirconium, tin, tantalum, titanium, gallium, antimony, and boron. Suitable halides are the fluorides, chlorides, and bromides. Representative of such metal halides include aluminum chloride, aluminum bromide, ferric chloride, ferric bromide, zirconium chloride, zirconium bromide, boron trifluoride, titanium tetrachloride, gallium chloride, tin tetrachloride, antimony fluoride, tantalum chloride, tantalum fluoride, and so forth. Of these metal halides the aluminum halides are preferred, especially aluminum chloride. Except for boron trifluoride, the chlorides are generally the preferable halides.

The reaction between the metal halides of this invention and the bound surface hydroxyl groups of the refractory inorganic oxide is readily accomplished by, for example, sublimation or distillation of the metal halide onto the surface of the particles of the metal inorganic oxide composite. The reaction is attended by the elimination of between about 0.5 and 2.0 moles of hydrogen halide per mole of metal halide adsorbed thereon. The reaction temperature will depend upon such variables as the reactivity of the metal halides and its sublimation temperature or boiling point, where the metal halide is reacted in the gas phase, as well as on the nature of the refractory inorganic oxide. For example, using aluminum chloride and alumina as our specific examples reaction readily occurs within the range between about 190° through 600° C.

The amount of metal halide which is reacted with the bound surface hydroxyl groups of the refractory inorganic oxide is generally given in terms of the weight percent of the Friedel-Crafts metal on the composite. This amount will vary with the refractory inorganic oxide used, the relative number of bound surface hydroxyls of the inorganic oxide (which may be related to the particular oxide phase utilized), the specific Friedel-Crafts metal halide employed, as well as the particular procedure used to effect reaction between the Friedel-Crafts type metal halide and the bound surface hydroxyl. As a rough rule of thumb for aluminum chloride on alumina, as an example, the amount of aluminum chloride reacted expressed as weight percent aluminum in the final composite ranges from about 0.1 up to about 2.5%, with the level being a function primarily of the number of bound surface hydroxyl groups on the refractory inorganic oxide.

The feedstock mixture of alkenes and alkanes is reacted with the catalytic composites of our invention at alkylation conditions. Such alkylation conditions include a temperature which may be as low as −10° C. and as high as 100° C., depending upon the particular feedstock used and the nature of the catalytic composite. Temperatures between about 10° and about 50° C. are preferred. Reaction pressures should be sufficient to maintain the reactants in a liquid phase but are not otherwise an important variable, that is, the pressure does not significantly influence the reaction other than maintaining the constituent in a liquid phase. Since the catalytic composite is employed as a bed with a liquid phase reactant mixture coming into contact with it, the liquid hourly space velocity of the feedstock is between 0.1 and about 5.0/hour, based on alkenes only.

As alluded to above, the alkylation reaction is performed as a continuous reaction in the liquid phase. The catalytic composite generally is present as a fixed bed although this is not a necessary limitation but rather merely represents a convenient reaction mode. A feedstock containing a mixture of alkenes having from 2 up through about 6 carbon atoms and alkanes having from 4 up through about 6 carbon atoms is passed in the liquid phase over the catalyst maintained at a temperature between about −10° and about 100° C. Although the reaction may be run in either an upflow or a downflow mode it is somewhat preferable to run this upflow, although this does not represent a strong preference. Preferred temperatures generally are in the range of 10°–50° C. and the feedstock is passed over the catalyst at a liquid hourly space velocity between about 0.1 and about 5.0/hr.

The prior basic description may be modified in ways well known to those skilled in the art. For example, a particularly desirable variant is one with staged olefin injection, sometimes referred to as interstage olefin injection. In this variant the initial feedstock entering the reaction zone contains a rather high ratio of alkane to alkene. Alkene is rapidly depleted to afford a feedstock very high in alkane content and additional amounts of alkene are injected at various points along the reaction zone. At each point the alkane/alkene ratio remains high because of the rapid depletion of alkene, although the overall alkane/alkene ratio remains between the stated limits of 100:1 to as low as perhaps 1:1, with the more frequently employed range being 20:1 to 5:1.

The following examples are merely illustrative of our invention and are not intended to limit it in any way.

EXAMPLES

Preparation of Catalysts. The following description is representative of catalyst preparation for materials whose test results are given in the following examples. An extruded precalcined gamma-alumina was impregnated with 0.25 weight percent platinum from an aqueous chloroplatinic acid solution in 2.5 weight percent hydrochloric acid. This material was then calcined at 500° C. in air for 3 hours prior to being impregnated with a metal cation of this invention. Where catalysts contained no metal having hydrogenation activity the aforedescribed steps are omitted.

Monovalent metal and/or alkali metal cations then were impregnated onto the aforementioned gamma-alumina. The amount of gram atoms of metal added contained the equivalent of 1 weight percent potassium in the case of the monovalent metal cations, and 0.5 weight percent potassium in the case of the alkaline earth metal cations. The monovalent metal or alkaline earth metal salts were added as aqueous solutions of the corresponding metal chlorides or metal nitrates to the gamma-alumina, and the mixture was continuously agitated during evaporation of water. After evaporation of water, the materials were dried at 150° C. for 2–4 hours, calcined at 500° C. for 3 hours, and finally were treated in a stream of flowing hydrogen at 500° C. for 3 hours to reduce the hydrogenation-active metal to its zerovalent state, which is its hydrogenation-active state.

The bound surface hydroxyl groups of the foregoing monovalent metal or alkaline earth metal impregnated alumina optionally containing a zerovalent metal having hydrogenation activity was then reacted with aluminum chloride via sublimation of the latter onto a hot surface of the composite performed as follows. A quartz tube containing the aforedescribed composite was loaded into a furnace and purged with nitrogen. The alumina composite then was heated to 260° C. in a flowing hydrogen stream followed by treatment with anhydrous HCl plus hydrogen for 40 minutes. At this time HCl flow was stopped, the temperature was raised to 500° C. in flowing hydrogen, and aluminum chloride contained in a separate flask attached to the quartz tube was heated to 200° C., which is above its sublimation temperature of 180° C. After the composite was at 500° C. for an additional hour it was cooled to 260° C. in flowing hydrogen and subsequently treated with a hydrogen-HCl mixture for one hour at 260° C. The resulting material was further cooled in a hydrogen atmosphere and finally in a nitrogen atmosphere. The final composite was stored under anhydrous nitrogen.

Alkylation test procedure. All tests were conducted using a fixed bed reactor operating in an upflow mode using a feedstock of isobutane and 2-butene in a molar ratio of 45. The 2-butene weight hourly space velocity was 0.2 hr$^{-1}$, the reaction temperature was 10° C., and the pressure was 450 psig.

EXAMPLE 1

Effects of various monovalent metal and alkaline earth metal cations. In this test the catalysts differed only in the nature of the metal cation impregnated thereon. Except for Example 2, all catalysts also contained zerovalent platinum. In all cases an alkylation run lasted for 1.5–2.0 hours. Results are summarized in Table 1.

TABLE 1

Effect of Alkali/Alkaline Earth Ions

| CATALYST (wt % alkali/alkaline earth metal, as cation) | INITIAL[a] RON | BEST[b] RON |
|---|---|---|
| No Alkali | 83 | 90 |
| No Alkali/No Pt | 83.5 | 90.2 |
| 0.81 Li | 90.5 | 94.0 |
| 0.59 Na | 92.0 | 95.5 |
| 1.00 K | 97.5 | 98.0 |
| 3.40 Cs | 94.0 | 97.0 |
| 0.31 Mg | 85.0 | 92.5 |
| 0.51 Ca | 86.5 | 93.0 |
| 2.76 Ag[c] | 90.1 | 91.2 |

[a]Research octane number measured 15 minutes into the run.
[b]Highest research octane number measured during the run.
[c]From AgNO$_3$ As the foregoing data show, in all cases addition of a monovalent metal or alkaline earth metal cation leads to a significant increase in product quality as measured by research octane number. Comparison of the first and second entries shows that Pt has virtually no effect on RON.

EXAMPLE 2

Effect of added potassium on various alkylation catalysts. This example compared various prior art-type catalysts with those of this invention containing 1 weight percent potassium as the cation. All catalysts also contained 0.25 weight percent zerovalent platinum. Results are summarized in Table 2.

TABLE 2

Effect of Potassium as Cation on Prior Art-Type Catalysts

| CATALYST[a]<br>(wt % alkali/alkaline<br>earth metal, as cation) | HOURS AT<br>100% CONV. | INITIAL[b]<br>RON | BEST[c]<br>RON |
|---|---|---|---|
| AlCl$_3$/No Metal | 2.0 | 83 | 90 |
| AlCl$_3$/1% K | 2.0 | 97.5 | 98.0 |
| BF$_3$/No Metal | 0.5 | 91.5 | 91.5 |
| BF$_3$/1.00 K | 0.5 | 94.3 | 94.8 |
| GaCl$_3$/No Metal | 2.0 | 84.0 | 93.0 |
| GaCl$_3$/1% K | 2 | 97.0 | 98.5 |
| AlBr$_3$/No Metal | 1.5–2.0 | 86.5 | 92.0 |
| AlBr$_3$/1% K | 2 | 97.5 | 98.5 |
| ZrCl$_4$/No Metal | 2 | 83.5 | 92.5 |
| ZrCl$_4$/1% K | 1.5–2.0 | 96.7 | 97.8 |

[a]All materials were composites with alumina as the refractory inorganic oxide and contained 0.25 weight percent Pt(O).
[b]Research octane number measured 15 minutes into the run.
[c]Highest research octane number measured during the run.

What Table 2 shows very clearly and very dramatically is that the presence of potassium, as representative of the alkali and alkaline earth cations, is effective in all cases, irrespective of the specific Friedel Crafts-type metal halide, although the magnitude of the effect does change with the particular metal halide employed.

EXAMPLE 3

Modified BF$_3$ on Alumina. The following are experimental data for the alkylation of butane using a feedstock of isobutane with 2-butene at a molar ratio of 95 and reaction conditions of 10° C., 450 psig, WHSV=0.2, similar to the conditions described in Example 1 of the application. The catalyst was prepared as generally described in the examples, with alumina as the support and boron trifluoride as the first metal halide. The RON is the research octane number measured 15 minutes into the run.

TABLE 3

Evaluation of Modified BF$_3$ on Alumina

| CATALYST | BF$_3$ ONLY | 0.25% Pt | 0.25 Pt/1% K |
|---|---|---|---|
| Minutes at 100% conversion | 30 | 30 | 30 |
| Conversion at 1 Hour | 80 | 90 | 92 |
| RON | 91.5 | 91.4 | 94.8 |
| Wt % 2,2,4-Trimethylpentane in Product | 55 | 55 | 69 |

The foregoing data show unequivocally that addition of a monovalent metal cation to the catalyst leads to a significant increase in product quality as measured by research octane number.

EXAMPLE 4

Trace Metal Analyses of Aluminas. Alumina samples used as catalyst supports were routinely analyzed for trace metals. Typical results for various types of aluminas are given below; the sample identified as "Kaiser" is a commercial alumina from Kaiser Alumina sold under the name Versal-250.

TABLE 4

Trace Metals in Alumina

| Metal (in ppm) | Sample A | Sample B | Sample C | Kaiser |
|---|---|---|---|---|
| Na | 98 | 20 | 23 | <1000 |
| Mg | <10 | 30 | <10 | <100 |
| Ca | <300 | <300 | <300 | <300 |
| Cu | <10 | <10 | | <10 |

Two types of commercial aluminas as well as an alumina routinely prepared for applicants were analyzed for trace metals by Galbraith Laboratories, an independent and well known analytical laboratory. Results obtained by them are found in Table 5. Catapal is a commercial alumina made by Vista. Versal-250 is a commercial alumina made by Kaiser Alumina; this sample is different from the one above. Sample D is an alumina routinely prepared by applicants' assignee.

TABLE 5

Trace Analyses by Independent Laboratory

| Metal (in ppm) | Catapal | Versal-250 | Sample D |
|---|---|---|---|
| Na | 1400 | 1850 | 1720 |
| K | 380 | 380 | 400 |
| Ca | <35 | 85 | 114 |
| Mg | <35 | <34 | <26 |

The foregoing data show the maximum amounts (in ppm) of trace metals in various types of commercial alumina is:
Na<2000 ppm
K≦400 ppm
Ca<300 ppm
Mg<35 ppm
Cu<10 ppm
These maximum levels are representative of those found in aluminas from various sources and demonstrate that the amounts added by applicants are far in excess of what may be reasonably expected to occur in merchant alumina.

What is claimed is:

1. A catalytic composite comprising: a) a refractory inorganic oxide, b) the reaction product of a first metal halide and bound surface hydroxyl groups of said refractory inorganic oxide, c) a second metal cation, and d) optionally a zerovalent third metal; where said refractory inorganic oxide is selected from the group consisting of alumina, titania, zirconia, chromia, silica, boria, silica-alumina, and combinations thereof; said first metal halide is a fluoride, chloride, or bromide and the first metal is selected from the group consisting of aluminum, gallium, zirconium and boron; said second metal cation is selected from the group consisting of i) monovalent metal cations in an amount from 0.0026 up to about 0.20 gram atoms per 100 grams refractory inorganic oxide for lithium, potassium, cesium, rubidium, silver, and copper, and in an amount from 0.012 to about 0.12 gram atoms for sodium, and (ii) alkaline earth metal cations in an amount from about 0.0013 up to about 0.01 gram atoms per 100 grams of refractory inorganic oxide for beryllium, strontium, and barium, and an amount from about 0.004 up to about 0.1 gram atoms per 100 grams support for magnesium and calcium; and any combination thereof; and said third metal is selected from the group consisting of platinum, palladium, nickel, ruthenium, rhodium, osmium and iridium, and any combination thereof.

2. The catalytic composite of claim 1 where the refractory inorganic oxide is alumina.

3. The catalytic composite of claim 2 where the alumina is a gamma, theta, or eta alumina.

4. The catalytic composite of claim 1 where the second metal cation is selected from the group consisting of lithium, sodium, potassium, cesium, rubidium, silver, copper(I), beryllium, magnesium, calcium, strontium and barium.

5. The catalytic composite of claim 1 where the second metal cation is an alkali metal cation.

6. The catalytic composite of claim 1 where the second metal is potassium.

7. The catalytic composite of claim 1 where the third metal is palladium, platinum, nickel, and combinations thereof.

8. A process for the alkylation of at least one alkene having from 2 to 6 carbon atoms with an alkane having from 4 to 6 carbon atoms to afford an alkylate of increased octane number comprising reacting in the liquid phase the alkene and alkane under alkylation conditions in the presence of a catalyst comprising: a) a refractory inorganic oxide, b) the reaction product of a first metal halide and bound surface hydroxyl groups of said refractory inorganic oxide, c) a second metal cation, and d) optionally a zerovalent third metal; where said refractory inorganic oxide is selected form the group consisting of alumina, titania, zirconia, chromia, silica, boria, silica-alumina, and combinations thereof; said first metal halide is a fluoride, chloride, or bromide and the first metal is selected form the group consisting of aluminum, gallium, zirconium and boron; said second metal cation is selected from the group consisting of i) monovalent metal cations in an amount from 0.0026 up to about 0.20 gram atoms per 100 grams refractory inorganic oxide for lithium, potassium, cesium, rubidium, silver, and copper and in an amount from 0.012 to about 0.12 gram atoms for sodium, and ii) alkaline earth metal cations in an amount from about 0.0013 up to about 0.01 gram atoms per 100 grams of refractory inorganic oxide for beryllium, strontium, and barium, and an amount from about 0.004 up to about 0.1 gram atoms per 100 grams support for magnesium and calcium; and any combination thereof; and said third metal is selected from the group consisting of platinum, palladium, nickel, ruthenium, rhodium, osmium and iridium, and any combination thereof; where the alkylate so formed has an increased octane number relative to alkylate formed in the absence of the second metal cation.

9. The process of claim 8 where the alkylation conditions include a molar ratio of alkane to alkene of from about 100:1 to about 1:1, a temperature from about −10° C. to about 100° C., and a pressure sufficient to ensure a liquid phase reaction.

10. The process of claim 8 where the refractory inorganic oxide is alumina.

11. The process of claim 10 where the alumina is a gamma, theta, or eta alumina.

12. The process of claim 8 where the alkane is isobutane.

13. The process of claim 8 where the alkene is a butene.

14. The process of claim 8 where the alkane is isobutane, at least one of the alkenes is a butene, the second metal halide is aluminum chloride, and the second metal cation is potassium.

15. The process of claim 14 where the refractory inorganic oxide is alumina.

16. The process of claim 8 where the alkane is isobutane, at least one of the alkenes is a butene, the second metal halide is aluminum chloride, and the second metal cation is an alkali metal cation.

* * * * *